US010058866B2

(12) United States Patent
Luoma, II et al.

(10) Patent No.: US 10,058,866 B2
(45) Date of Patent: Aug. 28, 2018

(54) METHODS AND APPARATUS TO MITIGATE BUBBLE FORMATION IN A LIQUID

(71) Applicants: Robert Paul Luoma, II, Colleyville, TX (US); Brian Ochranek, Southlake, TX (US); Cheryl L. Davidson, Southlake, TX (US); Bradley Weston, Frisco, TX (US)

(72) Inventors: Robert Paul Luoma, II, Colleyville, TX (US); Brian Ochranek, Southlake, TX (US); Cheryl L. Davidson, Southlake, TX (US); Bradley Weston, Frisco, TX (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/801,451

(22) Filed: Mar. 13, 2013

(65) Prior Publication Data

US 2014/0271411 A1    Sep. 18, 2014

(51) Int. Cl.
*B01L 3/00* (2006.01)
*B01L 3/12* (2006.01)
(Continued)

(52) U.S. Cl.
CPC ............... *B01L 3/52* (2013.01); *B01F 9/002* (2013.01); *B01F 9/003* (2013.01);
(Continued)

(58) Field of Classification Search
CPC .. B01L 3/52; B01L 3/5082; B01L 2200/0684; B01L 2300/0851; B01L 2400/086; B01F 9/002; B01F 9/003; B01F 11/0002; B01F 11/0005; B01F 11/0008; B01F 2009/0092; G01N 35/1002;
(Continued)

(56) References Cited

U.S. PATENT DOCUMENTS 423,362 A      3/1890  Wells
3,994,594 A *  11/1976 Sandrock et al. ............ 356/246
(Continued)

FOREIGN PATENT DOCUMENTS

CA     2556772     9/2005
CN     1183057     5/1998
(Continued)

OTHER PUBLICATIONS

International Search Report and Written Opinion, issued by the International Searching Authority in connection with corresponding International patent application No. PCT/US2013/078034, dated Sep. 12, 2014, 21 pages.
(Continued)

*Primary Examiner* — Robert Eom
(74) *Attorney, Agent, or Firm* — Hanley, Flight & Zimmerman, LLC

(57) ABSTRACT

Methods and apparatus to mitigate bubble formation in a liquid are disclosed. An example apparatus disclosed herein includes a bottom wall, a first baffle cantilevered from the bottom wall, and a second baffle cantilevered from the bottom wall. The first baffle is spaced apart from the second baffle, and the first baffle and the second baffle are positioned radially relative to an axis of rotation of the apparatus.

30 Claims, 8 Drawing Sheets

(51) Int. Cl.
  *B01L 3/14* (2006.01)
  *B01F 9/00* (2006.01)
  *B01F 11/00* (2006.01)
  *G01N 35/00* (2006.01)
  *G01N 35/04* (2006.01)
  *G01N 35/10* (2006.01)

(52) U.S. Cl.
  CPC ...... *B01F 11/0002* (2013.01); *B01F 11/0005* (2013.01); *B01F 11/0008* (2013.01); *B01L 3/5082* (2013.01); *G01N 35/1002* (2013.01); *B01F 2009/0092* (2013.01); *B01L 2200/0684* (2013.01); *B01L 2300/0851* (2013.01); *B01L 2400/086* (2013.01); *G01N 2035/00524* (2013.01); *G01N 2035/0439* (2013.01); *G01N 2035/1025* (2013.01)

(58) Field of Classification Search
  CPC . G01N 2035/00524; G01N 2035/0439; G01N 2035/1025
  See application file for complete search history.

(56) References Cited

U.S. PATENT DOCUMENTS

| | | | |
|---|---|---|---|
| D273,987 S | 5/1984 | Holen et al. | |
| 4,515,753 A | 5/1985 | Smith et al. | |
| 4,557,600 A * | 12/1985 | Klose | B04B 5/0407 356/246 |
| 4,684,614 A | 8/1987 | Krovak et al. | |
| 4,705,668 A | 11/1987 | Kaltenbach et al. | |
| D297,166 S | 8/1988 | Hollar et al. | |
| 4,849,177 A | 7/1989 | Jordan | |
| 4,883,763 A * | 11/1989 | Holen | B01L 3/50273 356/246 |
| 5,005,721 A | 4/1991 | Jordan | |
| 5,128,104 A | 7/1992 | Murphy et al. | |
| 5,324,481 A | 6/1994 | Dunn et al. | |
| D355,260 S | 2/1995 | Tomasso | |
| 5,417,922 A | 5/1995 | Markin et al. | |
| D365,153 S | 12/1995 | Robertson, Jr. | |
| 5,578,272 A | 11/1996 | Koch et al. | |
| 5,632,399 A | 5/1997 | Palmieri et al. | |
| 5,758,786 A | 6/1998 | John | |
| 5,788,928 A | 8/1998 | Carey et al. | |
| 5,811,296 A | 9/1998 | Chemelli et al. | |
| 5,830,411 A * | 11/1998 | Martinell Gisper-Sauch | 422/73 |
| D404,831 S | 1/1999 | Yamazaki et al. | |
| D411,014 S | 6/1999 | Berger et al. | |
| 5,968,453 A | 10/1999 | Shugart | |
| 6,066,300 A | 5/2000 | Carey et al. | |
| D433,149 S | 10/2000 | Fassbind et al. | |
| 6,149,872 A | 11/2000 | Mack et al. | |
| 6,190,617 B1 | 2/2001 | Clark et al. | |
| 6,190,619 B1 | 2/2001 | Kilcoin et al. | |
| 6,299,567 B1 | 10/2001 | Forrest et al. | |
| 6,319,719 B1 * | 11/2001 | Bhullar | B01L 3/502746 422/73 |
| 6,375,030 B1 | 4/2002 | Spickelmire | |
| 6,386,749 B1 | 5/2002 | Watts et al. | |
| 6,431,388 B1 | 8/2002 | Spicklemire et al. | |
| 6,432,359 B1 | 8/2002 | Carey et al. | |
| 6,458,526 B1 | 10/2002 | Schembri et al. | |
| 6,509,193 B1 | 1/2003 | Tajima | |
| 6,511,634 B1 | 1/2003 | Bradshaw et al. | |
| 6,517,783 B2 | 2/2003 | Horner et al. | |
| 6,537,505 B1 | 3/2003 | LaBudde et al. | |
| D482,454 S | 11/2003 | Gebrian | |
| 6,866,820 B1 | 3/2005 | Otto et al. | |
| D531,736 S | 11/2006 | Gomm et al. | |
| D532,524 S | 11/2006 | Gomm et al. | |
| D533,947 S | 12/2006 | Gomm et al. | |
| D534,280 S | 12/2006 | Gomm et al. | |
| 7,182,912 B2 | 2/2007 | Carey et al. | |
| 7,238,521 B2 | 7/2007 | Hahn et al. | |
| 7,458,483 B2 | 12/2008 | Luoma, II | |
| 7,485,118 B2 | 2/2009 | Blankenstein et al. | |
| 7,615,370 B2 | 11/2009 | Streit et al. | |
| 7,628,954 B2 | 12/2009 | Gomm et al. | |
| 7,731,414 B2 | 6/2010 | Vincent et al. | |
| 7,736,907 B2 * | 6/2010 | Blankenstein | B01L 3/502723 210/782 |
| D620,603 S | 7/2010 | Talmer et al. | |
| 7,794,656 B2 | 9/2010 | Liang et al. | |
| D630,765 S | 1/2011 | Winkenbach et al. | |
| D632,402 S | 2/2011 | Sattler et al. | |
| 7,897,379 B2 | 3/2011 | Kenney et al. | |
| D637,731 S | 5/2011 | Sattler et al. | |
| 7,951,344 B2 | 5/2011 | Kikuchi et al. | |
| 7,964,140 B2 | 6/2011 | Watari | |
| D645,973 S | 9/2011 | Hoenes | |
| 8,017,094 B2 | 9/2011 | Meyer et al. | |
| 8,133,721 B2 | 3/2012 | Yang et al. | |
| 8,187,558 B2 | 5/2012 | Jacobs et al. | |
| D665,095 S | 8/2012 | Wilson et al. | |
| D666,736 S | 9/2012 | Kobayashi | |
| D672,881 S | 12/2012 | Kraihanzel | |
| 8,535,624 B2 | 9/2013 | Luoma, II | |
| D696,419 S | 12/2013 | Fusellier et al. | |
| 9,149,979 B2 | 10/2015 | Sattler et al. | |
| 9,304,140 B2 | 4/2016 | Wakamiya | |
| 2002/0169518 A1 | 11/2002 | Luoma, II et al. | |
| 2003/0044323 A1 | 3/2003 | Diamond et al. | |
| 2003/0129766 A1 | 7/2003 | Kawamura et al. | |
| 2004/0005714 A1 | 1/2004 | Safar et al. | |
| 2004/0134750 A1 | 7/2004 | Luoma, II | |
| 2005/0106756 A1 * | 5/2005 | Blankenstein | B01L 3/502753 436/523 |
| 2006/0087911 A1 | 4/2006 | Herz et al. | |
| 2006/0263248 A1 | 11/2006 | Gomm et al. | |
| 2006/0286004 A1 | 12/2006 | Jacobs et al. | |
| 2007/0010019 A1 | 1/2007 | Luoma, II | |
| 2007/0166193 A1 | 7/2007 | Veen et al. | |
| 2008/0056948 A1 | 3/2008 | Dale et al. | |
| 2008/0064090 A1 | 3/2008 | Whittlinger | |
| 2008/0226513 A1 | 9/2008 | Morbidelli et al. | |
| 2008/0317632 A1 | 12/2008 | Shimasaki et al. | |
| 2009/0004058 A1 | 1/2009 | Liang et al. | |
| 2009/0215159 A1 | 8/2009 | Kirby | |
| 2009/0325309 A1 | 12/2009 | Favuzzi et al. | |
| 2010/0092343 A1 | 4/2010 | Ferenc Németh | |
| 2010/0111765 A1 | 5/2010 | Gomm et al. | |
| 2010/0190265 A1 | 7/2010 | Dufva et al. | |
| 2010/0276445 A1 | 11/2010 | Jacobs et al. | |
| 2012/0087830 A1 | 4/2012 | Wakamiya | |
| 2012/0141339 A1 | 6/2012 | Sattler et al. | |
| 2012/0195808 A1 | 8/2012 | Arras et al. | |
| 2012/0218854 A1 | 8/2012 | Behringer et al. | |
| 2013/0059376 A1 | 3/2013 | Justice et al. | |
| 2014/0038307 A1 | 2/2014 | Daub et al. | |
| 2015/0010443 A1 | 1/2015 | Hasegawa | |
| 2015/0224500 A1 | 8/2015 | Brueckner et al. | |

FOREIGN PATENT DOCUMENTS

| | | |
|---|---|---|
| CN | 1726288 | 1/2006 |
| CN | 101391197 | 3/2009 |
| CN | 101439274 | 5/2009 |
| CN | 101583877 | 11/2009 |
| CN | 102576030 | 12/2014 |
| EP | 0435481 | 7/1991 |
| EP | 0831330 | 3/1998 |
| EP | 1855114 | 11/2007 |
| EP | 1687080 | 6/2008 |
| EP | 1733794 | 9/2010 |
| EP | 2255880 | 12/2010 |
| GB | 1307086 | 2/1973 |
| JP | S527758 | 3/1977 |
| JP | S58134773 | 9/1983 |
| JP | H06253815 | 9/1994 |
| JP | H10228689 | 8/1998 |
| JP | H11515106 | 12/1999 |

(56) References Cited

FOREIGN PATENT DOCUMENTS

| JP | 2000009726 | 1/2000 |
|---|---|---|
| JP | 2005017176 | 6/2003 |
| JP | 2003194828 | 7/2003 |
| JP | 2004061160 | 2/2004 |
| JP | 2005502034 | 1/2005 |
| JP | 2005181338 | 7/2005 |
| JP | 2006125897 | 5/2006 |
| JP | 2007524842 | 8/2007 |
| JP | 2007309740 | 11/2007 |
| JP | 2008026221 | 2/2008 |
| JP | 4268212 | 5/2009 |
| JP | 2009276252 | 11/2009 |
| JP | 2009544959 | 12/2009 |
| WO | 9634681 | 11/1996 |
| WO | 03020427 | 3/2003 |
| WO | 2007125642 | 11/2007 |
| WO | 2008030961 | 3/2008 |
| WO | 2008058979 | 5/2008 |
| WO | 2009131705 | 10/2009 |
| WO | 2011091233 | 7/2011 |

OTHER PUBLICATIONS

Invitation to Pay Additional Fees and, Where Applicable, Protest Fee and Communication Relating to the Results of the Partial International Search, issued by the International Searching Authority in connection with corresponding International patent application No. PCT/US2013/078034, dated Jun. 3, 2014, 7 pages.
Isaacson et al., "Hydrodynamic damping due to baffles in a rectangular tank," Canadian Journal of Civic Engineering, Jul. 21, 2001, 9 pages.
Restriction and/or Election Requirement, issued by the United States Patent and Trademark Office in connection with U.S. Appl. No. 29/531,426 dated May 16, 2016, 9 pages.
Restriction and/or Election Requirement, issued by the United States Patent and Trademark Office in connection with U.S. Appl. No. 29/531,434 dated May 10, 2016, 8 pages.
Notification of Grant of Patent Right for a Design, issued by the State Intellectual Property Office of the P.R. China, in connection with Chinese Patent Application No. 201630099345.7, dated May 19, 2016, 5 pages.
Notification of Grant of Patent Right for a Design issued by the State Intellectual Property Office of the P.R. China, in connection with Chinese Patent Application No. 201630099342.3, dated May 19, 2016, 5 pages.
International Preliminary Report on Patentability and Written Opinion, issued by the International Searching Authority in connection with International patent application No. PCT/US2013/078034, dated Sep. 24, 2015, 15 pages.
Communication Pursuant to Rules 161 and 162 EPC, issued by the European Patent Office in connection with European Patent Application 13821411.9 dated Oct. 28, 2015, 2 pages.
Japanese Patent Office, "Notice of Rejection," issued in connection with Japanese Patent Application No. 2016-500148, dated Sep. 6, 2016, 11 pages.

Japanese Patent Office, "Notice of Rejection," issued in connection with Japanese Patent Application No. 5016-500147, dated Oct. 4, 2016, 8 pages.
First Office Action and Search Report issued by the State Intellectual Property Office of the P.R. China, in connection with Chinese Patent Application No. 201380076521.9, dated Jul. 13, 2016, 22 pages.
Requirement for Restriction/Election, issued by the United States Patent and Trademark Office in connection with U.S. Appl. No. 29/531,426, dated Aug. 18, 2016, 9 pages.
Restriction and/or Election Requirement, issued by the United States Patent and Trademark Office in connection with U.S. Appl. No. 29/531,434, dated Sep. 6, 2016, 9 pages.
State Intellectual Property Office of China, "Second Office Action," issued in connection with Chinese Patent Application No. 201380076521.9, dated Feb. 3, 2017, 23 pages.
State Intellectual Property Office of China, "First Office Action," issued in connection with Chinese Patent Application No. 201380076523.8, dated Oct. 18, 2016, 8 pages.
State Intellectual Property Office of China, "Third Office Action," issued in connection with Chinese Patent Application No. 201380076521.9, dated Jul. 28, 2017, 25 pages.
State Intellectual Property Office of China, "Second Office Action," issued in connection with Chinese Patent Application No. 201380076523.8, dated Jun. 12, 2017, 14 pages.
International Searching Authority, "International Search Report and Written Opinion," issued in connection with International Patent Application No. PCT/US2013/078036, dated Jun. 25, 2014, 17 pages.
International Searching Authority, "Invitation to Pay Additional Fees," issued in connection with International Patent Application No. PCT/US2013/078036, dated Apr. 23, 2014, 7 pages.
International Bureau, "International Preliminary Report on Patentability," issued in connection with International Patent Application No. PCT/US2013/078036, dated Sep. 24, 2015, 12 pages.
European Patent Office, "Communication pursuant to Rules 161(1) and 162 EPC," issued in connection with European Patent No. 13821412.7, dated Oct. 28, 2015, 2 pages.
United States Patent and Trademark Office, "Non-Final Office Action," issued in connection with U.S. Appl. No. 15/347,556, dated Mar. 7, 2017, 7 pages.
United States Patent and Trademark Office, "Notice of Allowance," issued in connection with U.S. Appl. No. 15/347,556, dated Jun. 14, 2017, 22 pages.
European Patent Office, "Communication pursuant to Article 94(3) EPC," issued in connection with European Patent No. 13 821 411.9, dated Jun. 7, 2017, 8 pages.
United States Patent and Trademark Office, "Ex parte Quayle Action," issued in connection with U.S. Appl. No. 29/531,434, dated Jan. 26, 2017, 15 pages.
United States Patent and Trademark Office, "Ex parte Quayle Action," issued in connection with U.S. Appl. No. 29/531,426, dated Dec. 30, 2016, 11 pages.
United States Patent and Trademark Office, "Notice of Non-Compliant Amendment," issued in connection with U.S. Appl. No. 29/531,426, dated Jun. 29, 2017, 15 pages.
United States Patent and Trademark Office, "Notice of Non-Compliant Amendment," issued in connection with U.S. Appl. No. 29/531,434, dated Jun. 29, 2017, 15 pages.

* cited by examiner

US 10,058,866 B2

METHODS AND APPARATUS TO MITIGATE BUBBLE FORMATION IN A LIQUID

FIELD OF THE DISCLOSURE

This disclosure relates generally to fluid analyzers and, more particularly, to methods and apparatus to mitigate bubble formation in a liquid.

BACKGROUND

Automated analyzers are used to analyze samples including biological material gathered from patients for diagnostic purposes. Generally, analysis of a sample involves reacting the sample with one or more reagents in a liquid container. Some automated analyzers store reagents in containers on a carousel. When a particular reagent is needed, the carousel is rotated to move the container holding the reagent to be adjacent an aspirating/dispensing device. The carousel moves by accelerating and decelerating, which subjects the reagents to rotational forces that could cause bubbles to form in the liquid.

Figure 1:
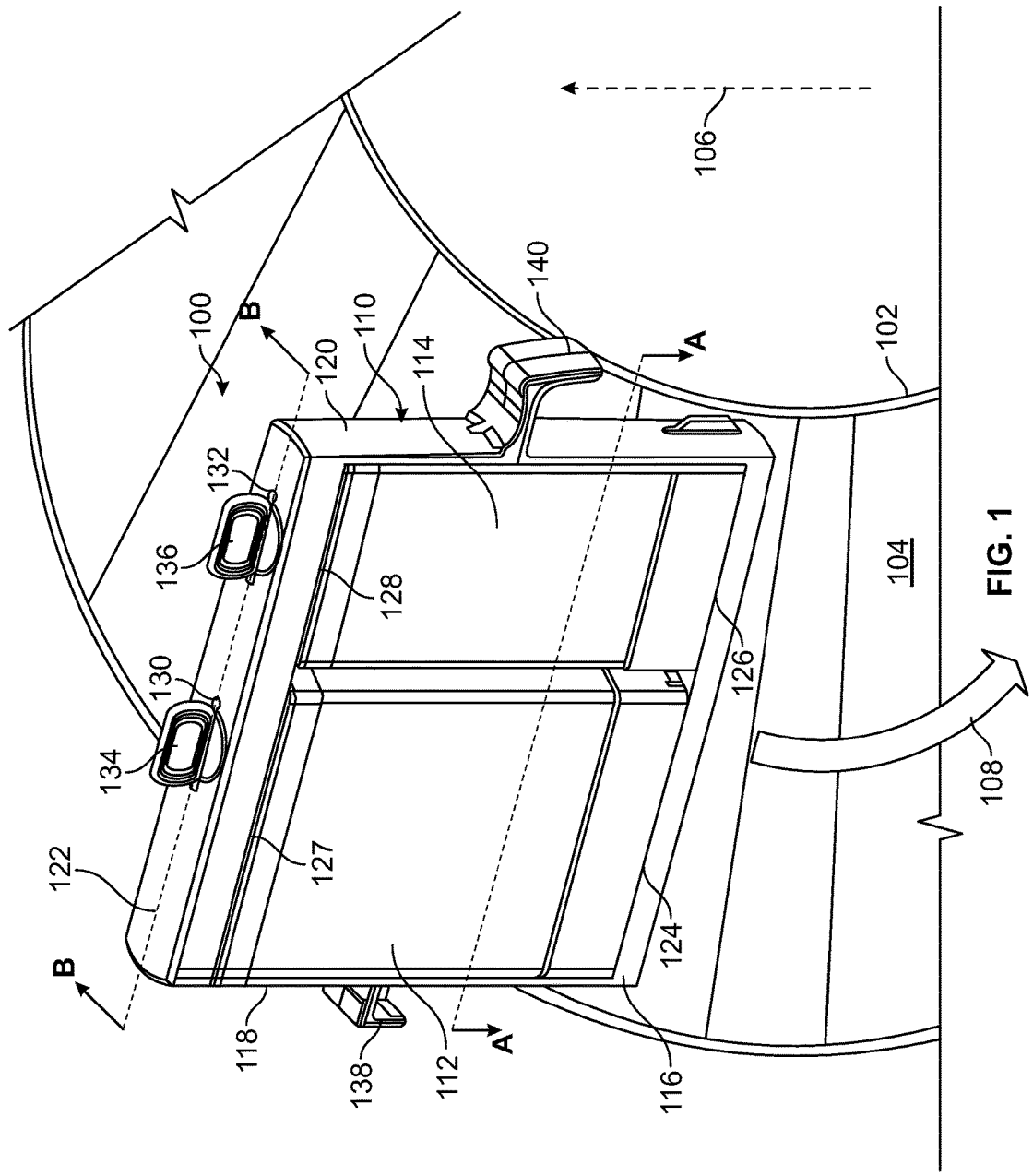
FIG. 1 illustrates an example cartridge that is holding a plurality of example containers and which is coupled to a portion of an example carousel.

Some of the figures or some of the portions of the figures may not be to scale. Instead, to clarify multiple layers and regions, the thickness of the layers may be enlarged in the drawings. Wherever possible, the same reference numbers will be used throughout the drawing(s) and accompanying written description to refer to the same or like parts. As used in this patent, stating that any part (e.g., a layer, film, area, or plate) is in any way positioned on (e.g., positioned on, located on, disposed on, or formed on, etc.) another part, means that the referenced part is either in contact with the other part, or that the referenced part is above the other part with one or more intermediate part(s) located therebetween. Stating that any part is in contact with another part means that there is no intermediate part between the two parts.

DETAILED DESCRIPTION

Disclosed herein are methods and apparatus to mitigate bubble formation in a liquid such as, for example, a liquid reagent in a container of an automatic diagnostic analyzer, which may be, for example, a clinical chemistry analyzer, an immunoassay analyzer, and/or a hematology analyzer. Some reagents used in automatic diagnostic analyzers include a liquid and one or more surfactants (e.g., detergents). Automatic diagnostic analyzers typically rotate reagent containers or bottles about an axis and/or in an oscillating manner, and the rotation, acceleration and/or deceleration imparts forces on the contents of the containers, which may agitate the contents of the containers.

When surfactants and/or reagents are agitated, bubbles and foam may form. Example containers disclosed herein use baffles to mitigate (e.g., reduce and/or substantially minimize) bubble formation in the liquid and enable the liquid to quickly settle after the containers decelerate to a substantially stationary state. Some example baffles disclosed herein extend from bottom walls of the containers and are spaced apart from sidewalls, end walls, and top walls of the containers. In some examples, the baffles are c-shaped and have concave portions facing an axis of rotation of the containers.

In the examples disclosed herein, the top walls define throats and crowns. When the example containers rotate, the liquid flows around the baffles and into the crowns without flowing into the throats and out of the containers. In some examples disclosed herein, the containers have rounded-rectangular shapes that provide greater space utilization in diagnostic systems than many known container configurations. As a result, using examples described herein, analyzers can have an increased load capacity and/or smaller size, compared to many known systems. The example containers can be created with fabrication techniques such as, for example, injection molding and/or laser welding, which reduce costs compared to the fabrication techniques used to create many known container configurations.

Disclosed herein is an example apparatus that includes a reagent container having a first sidewall and a second sidewall opposite the first sidewall. The example container further includes a top wall coupled to the first sidewall and the second sidewall. The example container also includes a bottom wall opposite the top wall, and the bottom wall is coupled to the first sidewall and the second sidewall. The example container also includes a first baffle extending from the bottom wall. The example first baffle is spaced apart from the first sidewall, the second sidewall, and the top wall.

In some examples, the apparatus also includes a second baffle extending from the bottom wall. The second baffle may be spaced apart from the first sidewall, the second sidewall, the top wall and the first baffle. In some examples, the first baffle has a first height and the second baffle has a second height greater than the first height. The first baffle and the second baffle may be positioned radially relative to an axis of rotation of the apparatus. In some examples, the first baffle has a c-shaped cross-section.

In some examples, the top wall includes a first portion and a second portion. The first portion may be at a first height relative to the bottom wall and the second portion may be at a second height relative to the bottom wall greater than the first height. In some examples, the first portion of the top wall defines an aperture. In some examples, the second portion of the top wall defines a crown, and liquid is to flow around the first baffle and into the crown when the apparatus is rotated.

In some examples, the apparatus also includes a carrier, and the container is removably coupled to the carrier. In some examples, the bottom wall is curved. In some examples, the apparatus also includes a first curved end wall and a second curved end wall opposite the first curved end wall. The first end wall and the second end wall may couple the first sidewall and the second sidewall.

Another example apparatus disclosed herein includes a bottom wall, a first baffle cantilevered from the bottom wall, and a second baffle cantilevered from the bottom wall. The example first baffle is spaced apart from the example second baffle, and the first baffle and the second baffle are positioned radially relative to an axis of rotation of the apparatus.

In some examples, the first baffle is curved. In some examples, the first baffle has a c-shaped cross-section and is oriented such that a concave portion of the c-shaped cross-section faces the axis of rotation of the apparatus. In some examples, the second baffle has a c-shaped cross-section and is oriented such that a concave portion of the c-shaped cross-section of the second baffle faces the axis of rotation of the apparatus.

Another example apparatus disclosed herein includes a bottom wall, a first sidewall coupled to the bottom wall, and a top wall coupled to the sidewall. The example top wall has a first portion and a second portion. The example first portion is at a first height relative to the bottom wall, and the example second portion is at a second height greater than the first height relative to the bottom wall. The example apparatus also includes a first baffle having a third height different than the first height and the second height. In some examples, the baffle extends from the bottom wall. In some examples, the third height is greater than the first height.

In some examples, the bottom wall, the first sidewall and the top wall define a chamber, and the first portion of the top wall comprises an aperture in fluid communication with the chamber.

In some examples, the first baffle is spaced apart from the first sidewall. In some examples, the apparatus also includes a second sidewall, and the first baffle is spaced apart from the second sidewall. The example apparatus may also include a first end wall and a second end wall opposite the first end wall. The first end wall and the second end wall may be coupled to the first sidewall and the second sidewall. In some examples, the first baffle is spaced apart from the first end wall and the second end wall. In some examples, a first distance between the first sidewall and the second sidewall adjacent the first end wall is less than a second distance between the first sidewall and the second sidewall adjacent the second end wall.

In some examples, the apparatus also includes a second baffle, and the first baffle and the second baffle are disposed radially relative to an axis of rotation of the apparatus. In some examples, the second baffle extends from the bottom wall. In some examples, the second baffle has a fourth height different than the first height, the second height and the third height. In some examples, the fourth height is less than the first height, and the third height is greater than the first height.

In some examples, the apparatus also includes a liquid reagent that may be disposed below the first height when the apparatus is stationary. In some examples, a portion of the liquid reagent is disposed between the first height and the second height during rotation of the example apparatus.

Also disclosed herein is an example method that includes rotating a container about an axis of rotation. In some examples, the container includes a bottom wall, a sidewall coupled to the bottom wall, and a top wall coupled to the sidewall opposite the bottom wall. An example top wall includes a first portion and a second portion. The first portion may be at a first height relative to the bottom wall, and the second portion may be at a second height greater than the first height relative to the bottom wall. The example second portion defines a crown. The example container also includes a first baffle coupled to the bottom wall and spaced apart from the sidewall and the top wall. The example container further includes a liquid. The example method also includes displacing the liquid around the first baffle during rotation, and displacing the liquid into a space defined by the crown during rotation.

In some examples, bubble formation in the liquid is decreased by the displacing of the liquid around the first baffle and the displacing of the liquid into the space defined by the crown. In some examples, the method also includes ceasing rotation and aspirating a portion of the liquid.

In some examples, the example method includes rotating the container with a substantially constantly changing velocity. Also, in some examples, the example method includes increasing a velocity of the container non-linearly over time and decreasing the velocity of the container nonlinearly over time.

Another example apparatus includes a container defining a chamber to hold a reagent. The example container includes a first sidewall, a second sidewall and a top wall. The example apparatus also includes a first baffle having a c-shaped cross-section disposed in the chamber. A first portion of the example first baffle is spaced apart from the top wall and at least one of the first sidewall or the second sidewall to enable a liquid in the chamber to flow around the first baffle to mitigate bubble formation in the liquid.

In some examples, a concave portion of the first baffle is to face an axis of rotation of the container. In some examples, the top wall defines a crown, and the first baffle extends into a space defined by the crown. In some examples, the apparatus also includes a second baffle having a c-shape cross-section, and the second baffle is disposed in the chamber. A second portion of the example second baffle may be spaced apart from the first baffle, the top wall and at least one of the first sidewall or the second sidewall.

In some examples, the first baffle and the second baffle are different heights. In some examples, the first baffle and the second baffle are positioned radially relative to an axis of rotation of the apparatus. The example apparatus may also include a first end wall and a second end wall coupled to the first sidewall and the second sidewall. The first portion of the first baffle may be spaced apart from the first end wall and the second end wall.

Turning now to the figures, FIG. 1 is a perspective view of an example cartridge 100 coupled to a carousel 102 of a diagnostic analyzer. In the illustrated example, the carousel 102 includes a platform 104 on which the cartridge 100 is supported. The cartridge 100 may be transported to and/or placed on the platform 104 manually, by a robotic device, via a conveyer, and/or via any other device and/or technique. During operation of the example carousel 102, the platform 104 and, thus, the cartridge 100 rotates about a first axis of rotation 106 along a substantially circular path 108 defined by the carousel 102. In some examples, multiple cartridges are coupled to the platform 104.

In some examples, the platform 104 periodically and/or aperiodically accelerates and decelerates while moving along a path 108 defined by the carousel 102. In the illustrated example, the path 108 is substantially circular. In other examples, the path 108 is other shapes. In some examples, the platform 104 moves periodically or aperiodically in one direction. In other examples, the platform 104 moves in a back-and-forth (e.g., oscillating) motion. For example, the platform 104 may repeatedly move a first distance in a first direction (e.g., clockwise) and then a second distance in a second direction (e.g., counterclockwise) opposite the first direction. In some examples, the distance moved in the first direction is greater than the distance moved in the second direction such that the cartridge 100 on the platform 104 oscillates via the back-and-forth motion while it revolves about the first axis of rotation 106. In some examples, after the platform 104 moves in the first direction, the platform 104 is substantially stationary for a given amount of time before moving in the second direction. In some examples, the first distance is approximately the same as the second distance such that the cartridge 100 moves to and from a given position on the path 108. Other examples move in other manners.

In the illustrated example, the cartridge 100 includes a base or carrier 110, a first container 112 and a second container 114. The example carrier 110 is coupled to the platform 104 to rotate with the platform 104. The example carrier 110 includes a seat 116, a first end wall 118, a second end wall 120 and a cover 122. In the illustrated example, first ends 124, 126 of the first container 112 and the second container 114, respectively, are coupled to the seat 116, and second ends 127, 128 of the first container 112 and the second container, respectively, are coupled to the cover 122.

In the illustrated example, the first container 112 and the second container 114 are arranged in the carrier 110 radially relative to the path 108 defined by carousel 102. In the illustrated example, the first container 112 is disposed adjacent the first end wall 118 and the second container 114 is disposed adjacent the second end wall 120. In some examples, the first container 112 and/or the second container 114 are rotatably coupled to the seat 116.

Figure 4:
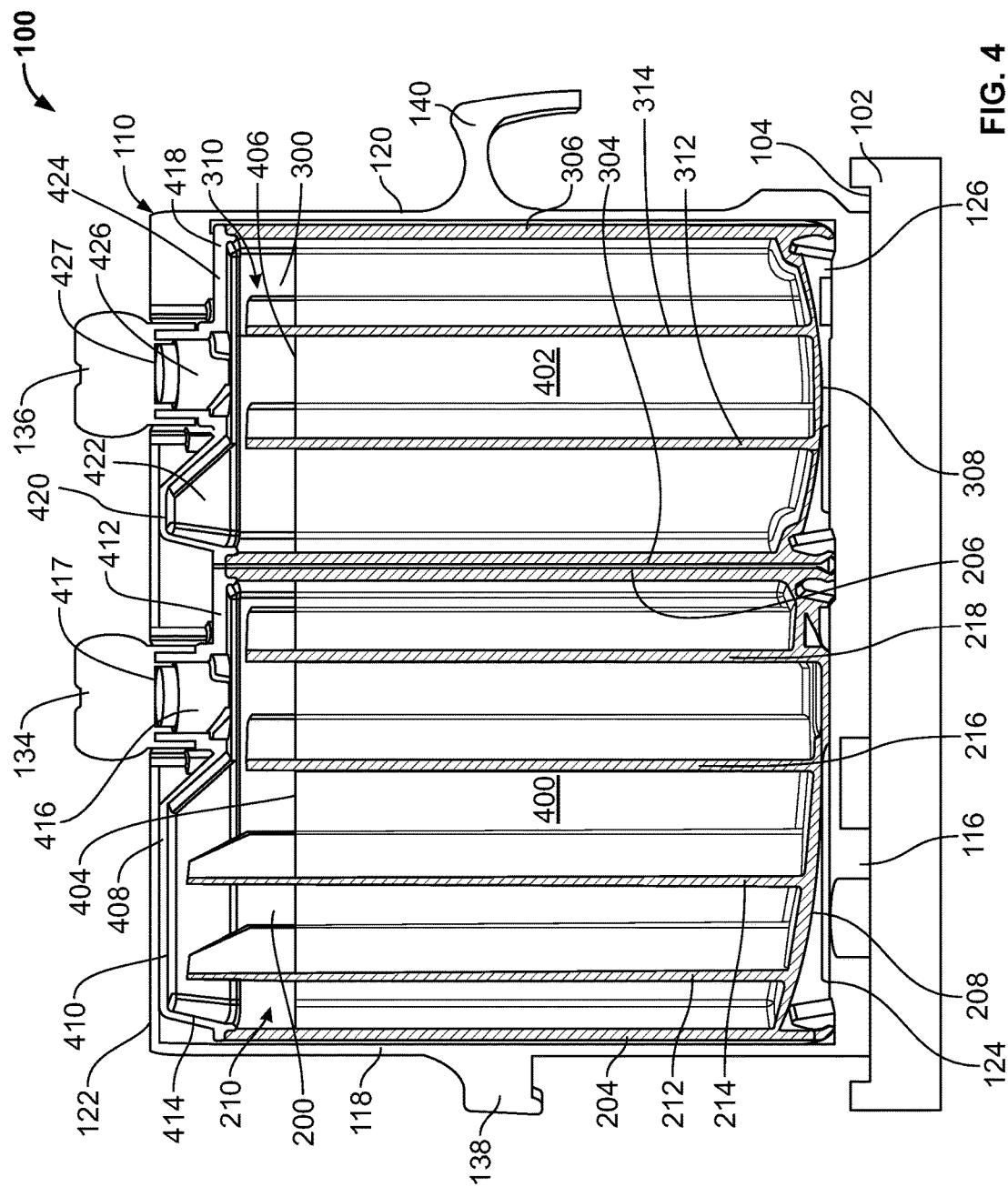
FIG. 4 is a side, cross-sectional view of the example cartridge of FIG. 1 taken along the B-B line of FIG. 1 when the example cartridge is substantially stationary.

Each of the containers 112, 114 is to hold a liquid 400, 402 (FIG. 4). In some examples, the liquids 400, 402 include a sample to be analyzed, one or more reagents, microparticles and/or surfactants (e.g., detergents). The example cover 122 includes a first aperture 130 and a second aperture 132 to provide access to the first container 112 and the second container 114, respectively. In the illustrated example, a first cap 134 is coupled to the first container 112, and a second cap 136 is coupled to the second container 114. The first cap 134 and the second cap 136 prevent the contents of the containers 112, 114 from flowing out of the containers 112, 114 when the cartridge 100 is being lifted, handled, maneuvered, transported, etc. In some examples, the caps 134, 136 are decoupled from the containers 112, 114 when the example cartridge 100 is disposed on the carousel 102. In some examples, the caps 134, 136 are decoupled from the containers 112, 114 prior to the example cartridge 100 being disposed on the carousel 102. In the illustrated example, the carrier 110 includes a first handle 138 and a second handle 140 to facilitate grasping, holding, lifting, maneuvering and/or transporting of the cartridge 100 by a human (e.g., manually) and/or a robot.

In the illustrated example, the first cap 134 extends out of the first aperture 130, and the second cap 136 extends out of the second aperture 132 to enable the first cap 134 and/or the second cap 136 to be removed from the first container 112 and the second container 114, respectively. When the first cap 134 and the second cap 136 are removed, the liquid may be deposited into and/or removed from the first container 112 and the second container 114. In some examples, a pipettor and/or other device(s) is inserted into the first container 112 and/or the second container 114 via the apertures 130, 132 to determine a liquid level inside, dispense a liquid into and/or aspirate a liquid from the first container 112 and/or the second container 114. As described in greater detail below, the example first container 112 and the example second container 114 mitigate (e.g., reduce and/or substantially minimize) bubble formation in the liquids 400, 402, thereby enabling accurate liquid level measurements to be taken via the pipettor and/or other device(s).

Figure 2:
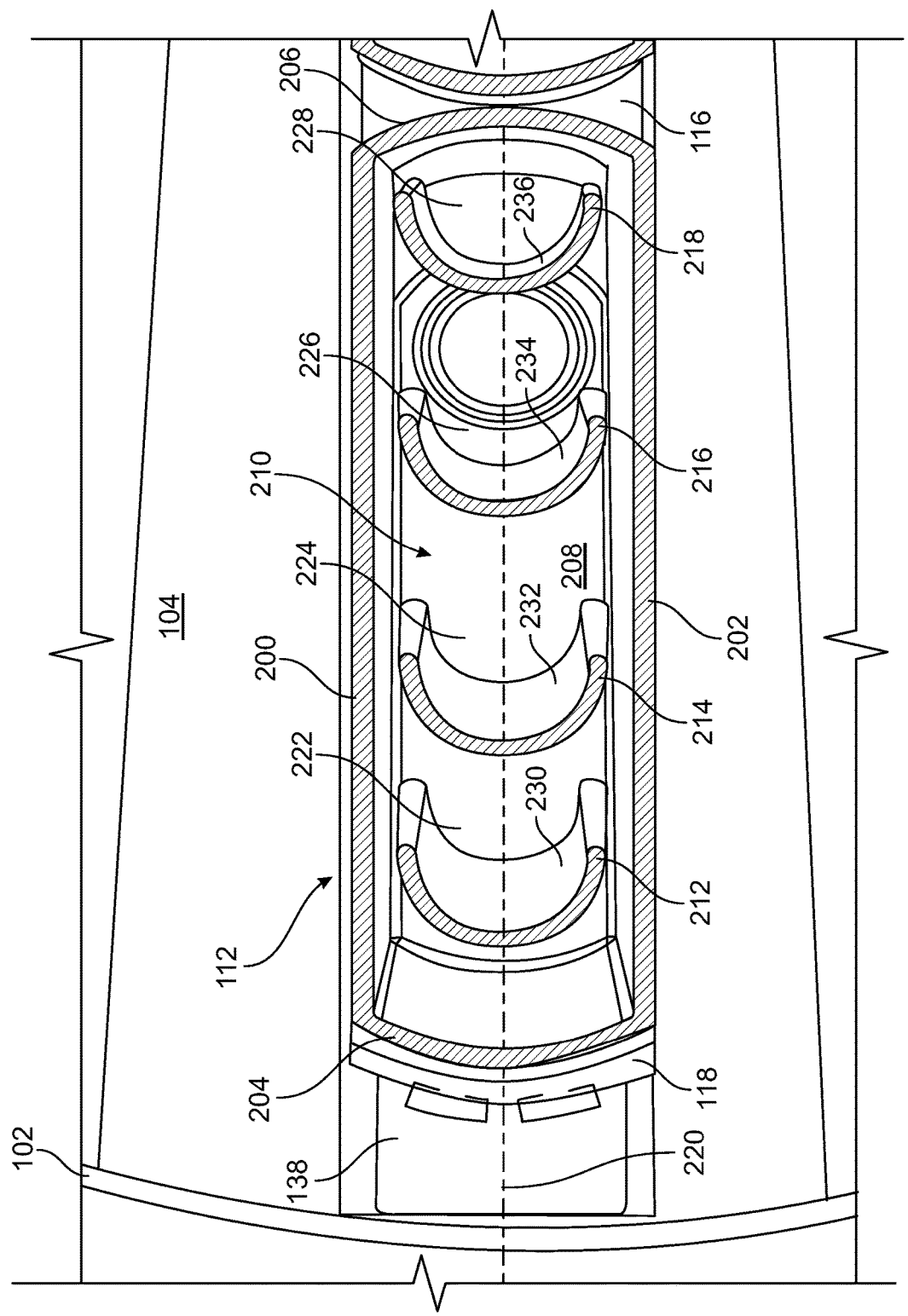
FIG. 2 is a cross-sectional view of a first container of the example cartridge of FIG. 1 taken along the A-A line of FIG. 1.

FIG. 2 is a cross-sectional view of the example first container 112 of FIG. 1 along line A-A of FIG. 1. In the illustrated example, the first container 112 includes a first sidewall 200, a second sidewall 202, a first end wall 204, a second end wall 206, a first bottom wall 208 and a first top wall 408 (FIG. 4) defining a first fluid chamber 210. The example first container 112 has a rounded-rectangular cross-sectional shape. In the illustrated example, the first sidewall 200 and the second sidewall 202 are substantially planar and parallel. The example first end wall 204 is opposite the example second end wall 206. In the illustrated example, the first end wall 204 and the example second end wall 206 couple the first sidewall 200 and the second sidewall 202 and are curved away from a central, longitudinal axis of the first container 112. In the illustrated example, a distance between the first sidewall 200 and the second sidewall 202 is less than a distance between the first end wall 204 and the second end wall 206. Other examples have other cross-sectional shapes (e.g., circular, elliptical, rectangular, square, polygonal, wedged, etc.).

In the illustrated example, the first container 112 includes a first baffle 212, a second baffle 214, a third baffle 216 and a fourth baffle 218 disposed inside the first fluid chamber 210. Other examples include other numbers of baffles (e.g., 1, 2, 3, 5, 6, etc.) In the illustrated example, the first baffle 212, the second baffle 214, the third baffle 216 and the fourth baffle 218 extend from the first bottom wall 208 toward the first top wall 408 (FIG. 4). In some examples, the baffles 212, 214, 216, 218 extend from the first bottom wall 208 substantially parallel to or otherwise aligned with each other. In some examples, the baffles 212, 214, 216, 218 extend from the first bottom wall 208 toward the first top wall 408 (FIG. 4) substantially parallel to or otherwise aligned with the axis of rotation 106 of the cartridge 100. In the illustrated example, the baffles 212, 214, 216, 218 are positioned along an axis 220 radially relative to the axis of rotation 106 of the example cartridge 100. The example baffles 212, 214, 216, 218 are spaced apart from each other along the axis 220. In some examples, the baffles 212, 214, 216, 218 are spaced apart from each other by substantially equal distances. In the illustrated example, the baffles 212, 214, 216, 218 are spaced apart by approximately 14 to 18 millimeters. In other examples, the baffles 212, 214, 216, 218 are equally spaced apart from each other by other distances. In some examples, the baffles 212, 214, 216, 218 are spaced apart from respective adjacent baffles by different distances. For example, the first baffle 212 and the second baffle 214 may be spaced apart a first distance, and the second baffle 214 and the third baffle 216 may be spaced apart a second distance, different than the first distance.

The example baffles 212, 214, 216, 218 are also spaced apart from the first sidewall 200, the second sidewall 202, the first end wall 204 and the second end wall 206. In the illustrated example, the baffles 212, 214, 216, 218 are spaced apart from the first side wall 200 by approximately one to two millimeters. The example baffles 212, 214, 216, 218 are also spaced apart from the second sidewall 202 by approximately one to two millimeters. Thus, in the illustrated example, the baffles 212, 214, 216, 218 are positioned approximately equidistant from the first sidewall 200 and the second sidewall 202. In other examples, the baffles 212, 214, 216, 218 are spaced apart from the first sidewall 200 and/or the second sidewall 202 by other distances. Also, in some examples, one or more of the baffles 212, 214, 216, 218 are spaced from one or both of the first and second sidewalls 200, 202 by distances different than other ones of the baffles 212, 214, 216, 218.

In the illustrated example, the baffles 212, 214, 216, 218 define respective channels 222, 224, 226, 228 facing the second end wall 206. Thus, when the example cartridge 100 is disposed on the carousel 102, the channels 222, 224, 226, 228 face the axis of rotation 106 of the cartridge 100. In the illustrated example, the baffles 212, 214, 216, 218 are curved such that the baffles 212, 214, 216, 218 have c-shaped (e.g., semi-circular) cross-sectional shapes and concave portions 230, 232, 234, 236 of the example baffles 212, 214, 216, 218 define the channels 222, 224, 226, 228. In the illustrated example, the baffles 212, 214, 216, 218 have substantially the same cross-sectional shape and size (e.g., radius of curvature and cross-sectional arc length). In other examples, the baffles 212, 214, 216, 218 have other cross-sectional shapes (e.g., crescent-shaped, a curved U-shape, an angled U-shape, etc.) and/or sizes. Also, in some examples, the baffles 212, 214, 216, 218 have shapes different from one or more of the other baffles 212, 214, 216 218. As described in greater detail below, the example baffles 212, 214, 216, 218 mitigate (e.g., reduce and/or minimize) bubble formation in the liquid 400, 402 inside the example first container 112.

Figure 3:
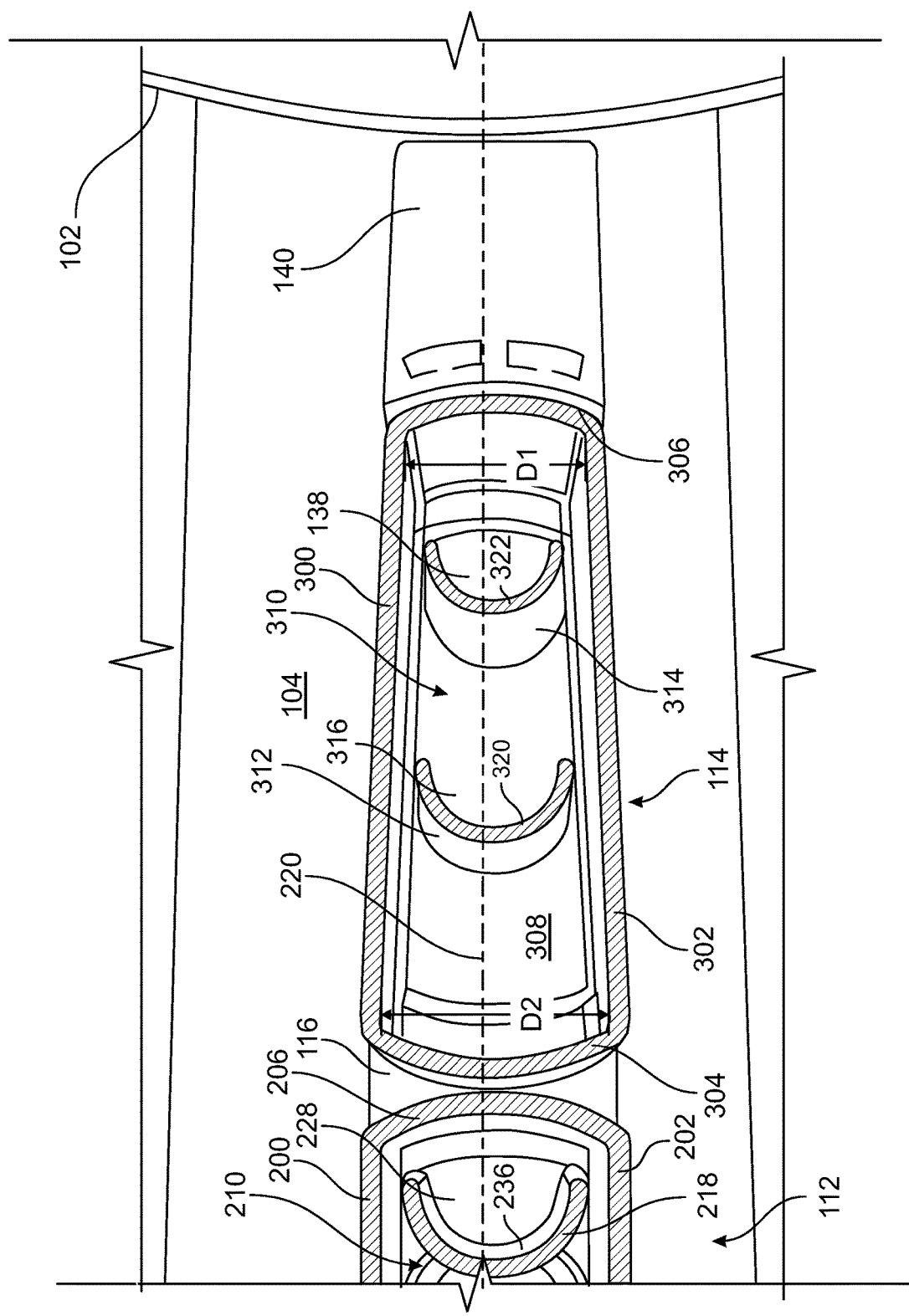
FIG. 3 is a cross-sectional view of a second container of the example cartridge of FIG. 1 taken along the A-A line of FIG. 1.

FIG. 3 is a cross-sectional view of the example second container 114 of FIG. 1 along line A-A of FIG. 1. In the illustrated example, the second container 114 includes a third sidewall 300, a fourth sidewall 302, a third end wall 304, a fourth end wall 306, a second bottom wall 308 and a second top wall 418 (FIG. 4) defining a second fluid chamber 310. The example second container 114 has a rounded-polygonal cross-sectional shape (e.g., a wedge shape). In the illustrated example, the third sidewall 300 and the fourth sidewall 302 are substantially planar and nonparallel. In the illustrated example, a first distance D1 between the third sidewall 300 and the fourth sidewall 302 adjacent the fourth end wall 306 is less than a second distance D2 between the third sidewall 300 and the fourth sidewall 302 adjacent the third end wall 304. The example third end wall 304 is opposite the example fourth end wall 306. In the illustrated example, the third end wall 304 and the fourth end wall 306 couple the third sidewall 300 and the fourth sidewall 302. In the illustrated example, the third end wall 304 and the example fourth end wall 306 are curved away from a central, longitudinal axis of the second container 114. In the illustrated example, the third end wall 304 has a greater cross-sectional arc length than the fourth end wall 306. Other examples have other cross-sectional shapes (e.g., circular, elliptical, rectangular, rounded rectangular, square, etc.) and/or sizes.

In the illustrated example, the second container 114 includes a fifth baffle 312 and a sixth baffle 314 disposed inside the second fluid chamber 310. Other examples include other numbers of baffles (e.g., 1, 3, 4, 5, 6, etc.) In the illustrated example, the fifth baffle 312 and the sixth baffle 314 extend from the second bottom wall 308 toward the second top wall 418 (FIG. 4). In some examples, the baffles 312, 314 extend from the second bottom wall 308 substantially parallel to each other. In some examples, the baffles 312, 314 extend from the second bottom wall 308 toward the second top wall 418 (FIG. 4) substantially parallel to the axis of rotation 106 of the cartridge 100. In the illustrated example, the baffles 312, 314 are positioned along the axis 220 radially relative to the axis of rotation 106. The example fifth baffle 312 is spaced apart from the example sixth baffle 314 along the axis 220. In the illustrated example, the baffles 312, 314 are spaced apart by approximately 14 to 18 millimeters. In other examples, the baffles 312, 314 are spaced apart from each other by other distances.

The example baffles 312, 314 of FIG. 3 are also spaced apart from the third sidewall 300, the fourth sidewall 302, the third end wall 304 and the fourth end wall 306. In the illustrated example, the baffles 312, 314 are spaced apart from the third side wall 300 by approximately one to two millimeters. The example baffles 312, 314 are also spaced apart from the fourth sidewall 302 by approximately one to two millimeters. Thus, in the illustrated example, the baffles 312, 314 are positioned approximately equidistant from the third sidewall 300 and the fourth sidewall 302. In other examples, the baffles 312, 314 are spaced apart from the third sidewall 300 and/or the fourth sidewall 302 by other distances. Also, in some examples, the fifth baffle 312 is spaced from the third sidewall 300 and/or fourth sidewall 302 a first distance, and the sixth baffle 314 is spaced from the third sidewall 300 and/or fourth sidewall 302 a second distance, different than the first distance.

In the illustrated example, the baffles 312, 314 each define a channel 316, 318 facing the fourth end wall 306. Thus, when the example cartridge 100 is disposed on the carousel 102, the channels 316, 318 face the axis of rotation 106 of the cartridge 100. In the illustrated example, the baffles 312, 314 are curved such that the baffles 312, 314 have c-shaped (e.g., semi-circular) cross-sectional shapes and concave portions 320, 322 of the example baffles 312, 314 define the channels 316, 318. In the illustrated example, the fifth baffle 312 has a greater cross-sectional size (e.g., arc length and radius of curvature) than the sixth baffle 314. In other examples, the baffles 312, 314 have other cross-sectional shapes (e.g., crescent-shaped, a curved U-shape, an angled U-shape, etc.) and/or sizes. Also, in some examples, the cross-sectional shapes of the baffles 312, 314 do not match. As described in greater detail below, the example baffles 312, 314 mitigate (e.g., reduce and/or minimize) bubble formation in the liquid 402 inside the example second container 114.

FIG. 4 is a cross-sectional view of the example cartridge 100 along line B-B of FIG. 1. In the illustrated example, the first container 112 contains the first liquid 400, and the second container 114 contains the second liquid 402. In the illustrated example, the first container 112 has a different liquid volume capacity than the second container 114. In the illustrated example, ninety percent of the volume of the first fluid chamber 210 of the example first container 112 is filled with the first liquid 400 and, thus, the first container 112 contains approximately 75 milliliters of the first liquid 400. Ninety percent of the volume of the example second fluid chamber 310 of the second container 114 is filled with the second liquid 402 and, thus, the second container 114 contains approximately 47 milliliters of the second liquid 402. In the illustrated example, the cartridge 100 is substantially stationary and, thus, the first liquid 400 and the second liquid 402 are substantially level (e.g., a first surface 404 and a second surface 406 of the first liquid 400 and the second liquid 402, respectively, are substantially horizontal).

In the illustrated example, the first top wall 408 of the first container 112 is coupled to the first sidewall 200, the second sidewall 202, the first end wall 204 and the second end wall 206 and has a first portion 410 adjacent the first end wall 204 and a second portion 412 adjacent the second end wall 206. In the illustrated example, the top wall 408 is stepped such that the first portion 410 of the first top wall 408 is a first height or distance from the first bottom wall 208, and the second portion 412 of the first top wall 408 is a second height or distance, which is less than the first height or distance from the first bottom wall 208. Thus, the first portion 410 of the example top wall 408 defines a first crown 414. In some examples, the crown 414 may be dome shaped. When the example first fluid 400 is substantially level, an amount of space between the first fluid 400 and the first portion 410 of the first top wall 408 is greater than an amount of space between the first fluid 400 and the second portion 412 of the first top wall 408. As described in greater detail below, the first crown 414 provides a space for the first liquid 400 to flow into when the example cartridge 100 is rotating.

In the illustrated example, the second portion 412 of the first top wall 408 includes a first throat 416. The example first throat 416 is in fluid communication with the first fluid chamber 210. In the illustrated example, the first cap 134 is coupled to the first throat 416 to cover and/or seal an aperture 417 defined by the first throat 416. When the example first cap 134 is removed, a sample and/or a liquid may be dispensed and/or removed (e.g., aspirated) from the first container 112 via the first throat 416, a volume of the first liquid 400 may be determined via a tool (e.g., a pipettor) extending into the first fluid chamber 210 via the first throat 416, etc.

In the illustrated example, the first baffle 212 and the second baffle 214 are positioned between the first bottom wall 208 and the first portion 410 of the first top wall 408. The example first baffle 212 and the example second baffle 214 are a third height, which is less than the first height of the first portion 410 of the first top wall 408 and greater than the second height of the second portion 412 of the first top wall 408 relative to the first bottom wall 208. Thus, the first baffle 212 and the second baffle 214 extend from the first bottom wall 208 into a space defined by the first crown 414 of the first top wall 408. The first baffle 212 and second baffle 214 do not contact the first top wall 408, and thus, the first baffle 212 and the second baffle 214 of the illustrated example are cantilevered from the first bottom wall 208.

In the illustrated example, the third baffle 216 and the fourth baffle 218 are positioned between the first bottom wall 208 and the second portion 412 of the first top wall 408. In the illustrated example, the third baffle 216 and the fourth baffle 218 are a fourth height, which is less than the second height of the second portion 412 of the first top wall 408. The third baffle 214 and the fourth baffle 216 do not contact the first top wall 408 and, thus, the example third baffle 216 and the example fourth baffle 218 are also cantilevered from the first bottom wall 208. In the illustrated example, the first baffle 212 and the second baffle 214 extend farther from the first bottom wall 208 than the third baffle 216 and the fourth baffle 216. In some examples, the baffles 212, 214, 216, 218 are other heights relative the first bottom wall 208. Also, in the illustrated example, the first bottom wall 208 is curved away from the first top wall 408 (e.g., concave relative to the top wall 408) to increase a fluid volume capacity and/or to minimize dead volume (e.g., volume not filled with fluid and, thus, not available for aspiration) of the first container 112. In other examples, the first bottom wall 208 is other shapes (e.g., substantially straight or flat, etc.)

The second top wall 418 of the example second container 114 includes a third portion 420 defining a second crown 422 and a fourth portion 424 including a second throat 426. In some examples, the second crown 422 is dome shaped. In the illustrated example, the third portion 420 of the example second top wall 418 is adjacent the third end wall 304 and the fourth portion 424 is adjacent the fourth end wall 306. In the illustrated example, the second top wall 418 is stepped such that the third portion 420 of the first top wall 418 is the first height from the second bottom wall 308, and the fourth portion 424 of the second top wall 418 is the second height, which is less than the first height from the second bottom wall 308. When the example second fluid 402 is substantially level, an amount of space between the second fluid 402 and the third portion 420 of the second top wall 418 is greater than an amount of space between the second fluid 402 and the fourth portion 424 of the second top wall 418. As described in greater detail below, the second crown 422 provides a space for the second liquid 402 to flow into when the example cartridge 100 is rotating.

In the illustrated example, the example second throat 426 is in fluid communication with the second fluid chamber 310 of the second container 114. In the illustrated example, the second cap 136 is coupled to the second throat 426 to cover and/or seal an aperture 427 defined by the second throat 426. When the example second cap 136 is removed, a sample and/or a liquid may be dispensed and/or removed (e.g., aspirated) from the second container 114 via the second throat 426, a volume of the second liquid 402 may be determined via a tool (e.g., a pipettor) extending into the second fluid chamber 310 via the second throat 426, etc. In the illustrated example, the second bottom wall 308 is curved away from the second top wall 418 (e.g., concave relative to the second top wall 418) to increase a fluid volume capacity of the example second container 114. In other examples, the second bottom wall 308 is other shapes (e.g., straight or flat, etc.).

In the illustrated example, the fifth baffle 312 and the example sixth baffle 314 are cantilevered from the second bottom wall 308. In the illustrated example, the fifth baffle 312 and the sixth baffle 314 are positioned between the second bottom wall 308 and the fourth portion 424 of the second top wall 418. In the illustrated example, the fourth baffle 312 and the fifth baffle 314 are the fourth height and do not contact the second top wall 418. In some examples, the baffles 312, 314 are other heights relative the second bottom wall 308.

Figure 5:
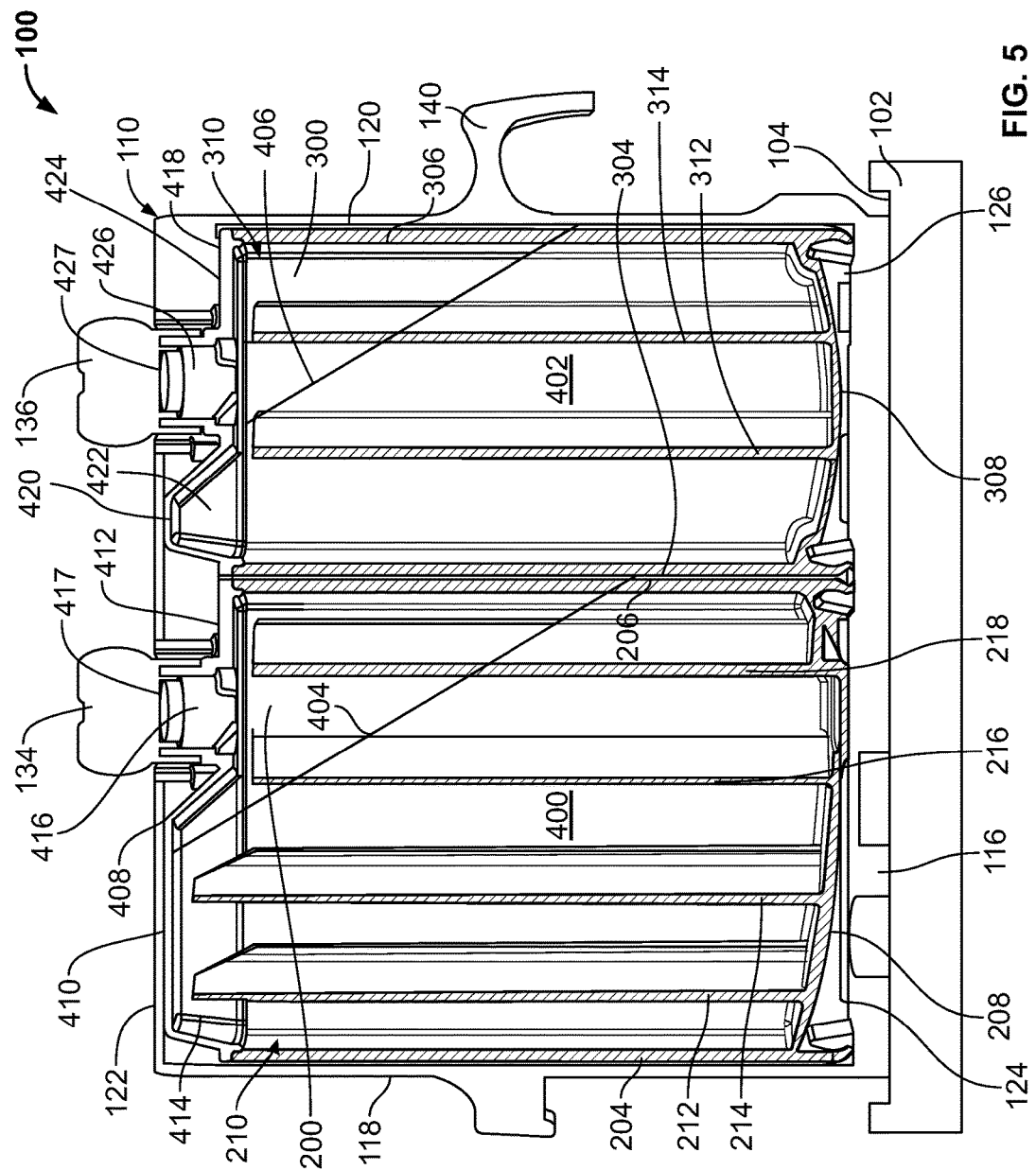
FIG. 5 is a side, cross-sectional view of the example cartridge of FIG. 1 taken along the B-B line of FIG. 1 when the example cartridge is rotating.

FIG. 5 is a cross-sectional view of the example cartridge 100 of FIGS. 1-4 along line B-B of FIG. 1 when the example cartridge 100 is rotating about the axis of rotation 106. When the example cartridge 100 is rotating about the axis of rotation 106, centrifugal forces urges the first liquid 400 and the second liquid 402 away from the axis of rotation 106. In the illustrated example, the first container 112 is positioned on the platform 104 such that the first crown 414 is disposed farther away from the axis of rotation 106 than the first throat 416. Similarly, the example second container 114 is positioned on the platform 104 such that the second crown 422 is positioned farther away from the axis of rotation 106 than the second throat 426. As a result, when the example cartridge 100 rotates, the first liquid 400 flows around the baffles 212, 214, 216, 218 and into the space in the first fluid chamber 210 defined by first crown 414, and the second liquid 402 flows around the baffles 312, 314 and into the space in the second fluid chamber 310 defined by the second crown 422. As a result, the liquid 400, 402 is displaced such that the first surface 404 of the first liquid 400 and the second surface 406 of the second liquid 402 are slanted or angled relative to the horizontal but the first liquid 400 and the second liquid 402 do not flow into the first throat 416 and the second throat 426, respectively, as the example cartridge 100 moves along the path 108 defined by the carousel 102. In the illustrated example, a portion of each of the liquids 400, 402 is disposed between the first height and the second height during rotation of the example cartridge 100. In addition, the extension of the first baffle 212 and the second baffle 214 into the first crown 414, function to further mitigate bubble formation on the liquid in the first container 112 as the first container 112 is rotated and liquid is disposed into the first crown 414.

In some examples, the cartridge 100 is periodically or aperiodically accelerated and decelerated as the cartridge 100 moves along the path 108. As a result, the first liquid 400 and the second liquid 402 flow in and out of the spaces defined by the first crown 414 and the second crown 422, respectively. The example baffles 212, 214, 216, 218, 312, 314 of the first container 112 and the second container 114 dampen or reduce the flow (e.g., sloshing) of the liquid 400, 402 as the liquid 400, 402 flows around the baffles 212, 214, 216, 218, 312, 314. As a result, the baffles 212, 214, 216, 218 mitigate (e.g., reduce and/or minimize) bubble formation in the first liquid 400 and the second liquid 402. In some examples, when the cartridge 100 decelerates to a stationary state, the first liquid 400 and the second liquid 402 flow from the spaces defined by the crowns 414, 422 to a substantially settled and/or level position (e.g., where the surfaces 404, 406 of the first liquid 400 and the second liquid 402 are substantially horizontal within approximately 100 to 300 milliseconds of the cartridge 100 being stationary.

Figure 6:
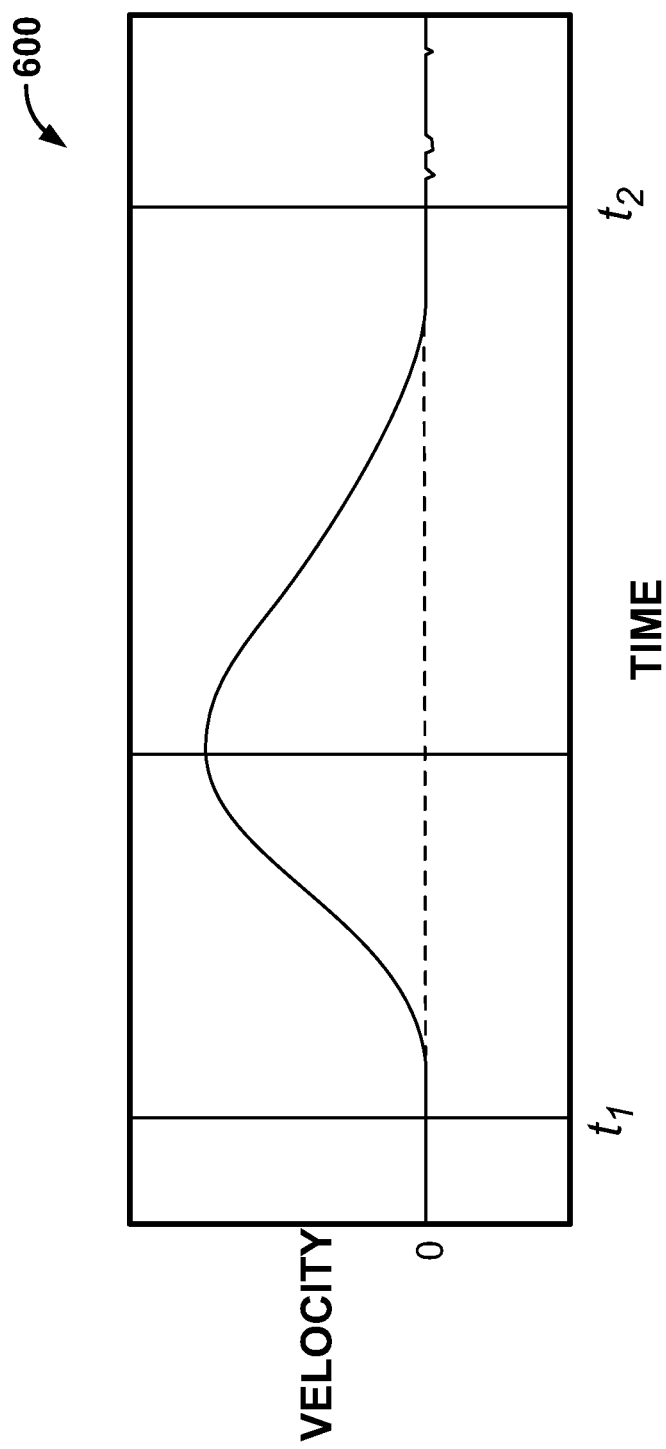
FIG. 6 is a graph showing a velocity of the example cartridge on the carousel of FIG. 1 over a period of time.

FIG. 6 is a graph 600 illustrating a velocity of the example cartridge 100 over time. In the illustrated example, between a first time $t_1$ and a second time $t_2$, the example cartridge 100 moves from a first position to a second position along the path 108. In the illustrated example, the first position and the second position are approximately 180 degrees apart along the path 108, and the second time $t_2$ is one second after the first time $t_1$. Thus, in the illustrated example, the cartridge 100 moves 180 degrees around the example path 108 in one second. In other examples, the cartridge 100 moves other numbers of degrees (e.g., 45 degrees, 90 degrees, 360 degrees, etc.) in one second or in other amounts of time.

In the illustrated example, the cartridge 100 is in the stationary state (e.g., at a velocity of substantially zero) at the first time $t_1$ and at the second time $t_2$. Thus, in some examples, the liquid 400, 402 is substantially level at the first time $t_1$. Beginning at the first time $t_1$, the example cartridge 100 accelerates from a velocity of approximately zero to a peak velocity (e.g., a maximum velocity of the cartridge 100 between the first time $t_1$ and second time) and then decelerates from the peak velocity to a velocity of approximately zero. In the illustrated example, the example cartridge 100 accelerates from a velocity of zero to the peak velocity in approximately 0.4 seconds. The example cartridge 100 then, in this example, decelerates from the peak velocity to a velocity of zero in approximately 0.6 seconds. Thus, the example cartridge 100 accelerates during an initial 40 percent of the movement of the cartridge 100 from the first position to the second position and decelerates during a latter 60 percent of the movement. In the illustrated example, between the first time $t_1$ and the second time $t_2$, the example cartridge 100 substantially does not move at a constant velocity.

When the example cartridge 100 accelerates to the peak velocity, the first liquid 400 flows around the baffles 212, 214, 216, 218 and into the space in the first fluid chamber 210 defined by first crown 414, and the second liquid 402 flows around the baffles 312, 314 and into the space in the second fluid chamber 310 defined by the second crown 422. As a result, the liquid 400, 402 is displaced such that the first surface 404 of the first liquid 400 and the second surface 406 of the second liquid 402 are slanted or angled relative to the horizontal or otherwise not horizontal, but the first liquid 400 and the second liquid 402 do not flow into the first throat 416 and the second throat 426, respectively, as the example cartridge 100 accelerates from the first position.

As the example cartridge 100 decelerates from the peak velocity, the fluid 400, 402 flows out of the spaces defined by the crowns 414, 422, and the example baffles 212, 214, 216, 218, 312, 314 of the first container 112 and the second container 114 dampen or reduce the flow (e.g., sloshing) of the liquid 400, 402 as the liquid 400, 402 approaches and reaches a velocity of zero at the second time t2. The example baffles 212, 214, 216, 218 mitigate (e.g., reduce and/or minimize) bubble formation in the first liquid 400 and the second liquid 402 as the example cartridge 100 moves from the first position to the second position. As a result, after the cartridge 100 reaches the second position at the second time t2 and, thus, is in the stationary state, the first liquid 400 and the second liquid 402 settle to a level position (e.g., where the surfaces 404, 406 of the first liquid 400 and the second liquid 402 are substantially horizontal) within, in this example, approximately 100 to 300 milliseconds after the second time t2. Thus, the baffles promote quick settling time. A faster settling time allows the carousel 102 holding the cartridge 100 to be rotated at a faster rate, which allows the system or analyzer into which these components are incorporated to achieve a higher throughput. Higher throughput improves lab productivity.

Also, as shown in FIG. 6, the motion curves are smooth and lack significant jerk (e.g., rates of change of acceleration/deceleration that may be illustrated with a velocity profile having transition points representing discontinuities in an acceleration profile).

Figure 7:
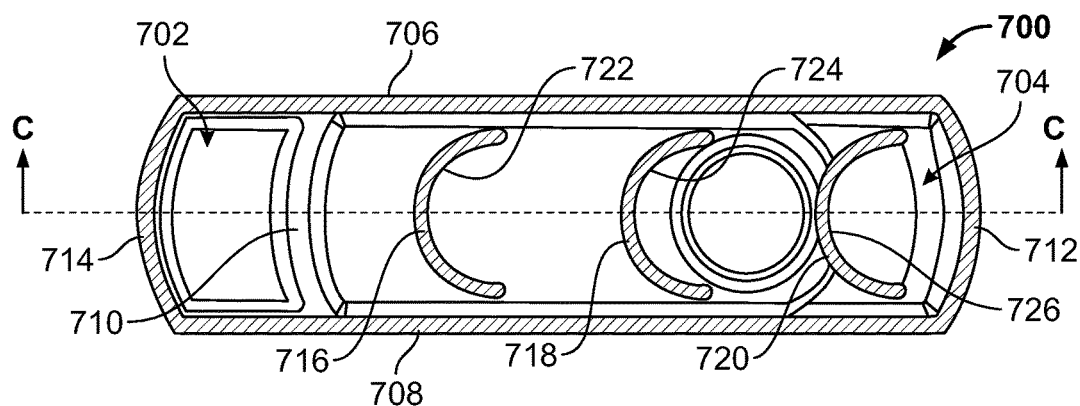
FIG. 7 is a top, cross-sectional view of an alternative example container disclosed herein.

FIG. 7 is a top, cross-sectional view of another example container 700 disclosed herein, which may be used to implement the example cartridge 100 of FIG. 1. In the illustrated example, the container 700 includes a first chamber 702 and a second chamber 704. The example first chamber 702 is to be substantially empty (e.g., not filled with a liquid). A portion (e.g., ninety percent) of the volume of the example second chamber 704 is to be filled with a liquid such as, for example, a reagent, microparticles, one or more surfactants (e.g., a detergent), etc. Other examples have other shapes.

The example second chamber 704 is defined by a first sidewall 706, a second sidewall 708, a first end wall 710 and a second end wall 712. The example first end wall 710 separates the first chamber 702 from the second chamber 704. The first chamber 702 is defined by the first sidewall 706, the second sidewall 708, the first end wall 710 and a third end wall 714. In the illustrated example, the container 700 has a rounded-rectangular perimeter shape, and the second chamber 704 has a substantially rounded-rectangular shape from the perspective of FIG. 7.

In the illustrated example, a first baffle 716, a second baffle 718 and a third baffle 720 are disposed in the second chamber 704. In the illustrated example, the baffles 716, 718, 720 are c-shaped and are oriented such that concave portions 722, 724, 726 of the baffles 716, 718, 720 face the axis of rotation 106 when the container 700 is positioned on the platform 104 via the cartridge 100. The example baffles 716, 718, 720 are spaced apart from each other and the walls 706, 708, 710, 712 defining the second chamber 704.

Figure 8:
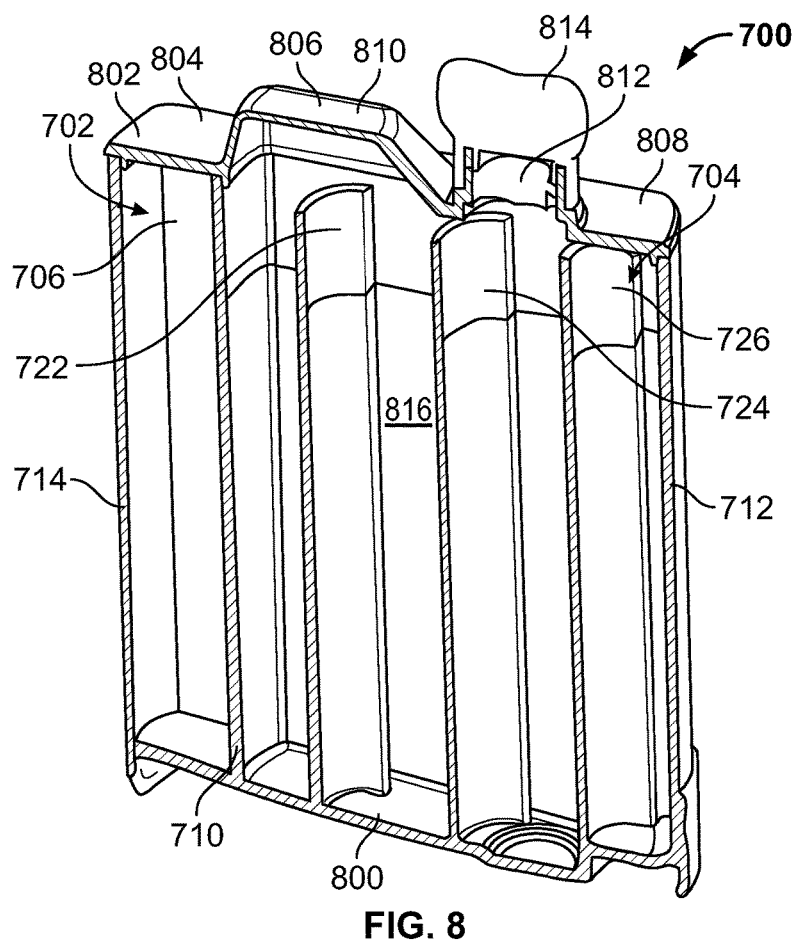
FIG. 8 is a perspective, cross-sectional view of the example container of FIG. 7 taken along the C-C line of FIG. 7.

FIG. 8 is a perspective, cross-sectional view of the example container 700 along line C-C of FIG. 7. In the illustrated example, the baffles 716, 718, 720 extend from a bottom wall 800 of the container 700 toward a top wall 802 of the container 700. The example baffles 716, 718, 720 do not contact the top wall 802. In the illustrated example, the baffles 716, 718, 720 extend from the bottom wall 800 to a first height below the top wall 802 in the orientation of FIG. 8.

The example top wall 802 includes a first portion 804, a second portion 806 and a third portion 808. In the illustrated example, the first portion 804 and the third portion 808 of the top wall 802 are at a second height relative to the bottom wall 800 greater than the first height of the baffles 716, 718, 720. The example second portion 806 of the top wall 802 is stepped from the first portion 804 and the third portion 808 to define a crown 810 having a third height greater than the first height and the second height. In the illustrated example, the second portion 806 of the top wall 802 is between the first portion 804 and the third portion 808. In the illustrated example, the third portion includes a throat 812, which is covered and/or sealed by a cap 814. When the cap 814 is removed, a sample and/or a liquid (e.g., one or more reagents, surfactants, etc.) may be dispensed and/or aspirated via the throat 812.

When the example container 700 is moved (e.g., accelerated and decelerated, for example, as illustrated in the graph 600 of FIG. 6) along the path 108, a liquid 816 (e.g., one or more reagents, surfactants, etc.) disposed in the second chamber 704 around the baffles 716, 718, 720 and in and out of a space defined by the crown 810 without flowing out of the container 700 via the throat 812. The example baffles 716, 718, 720 dampen the flow (e.g., sloshing) of the liquid 816 to mitigate (e.g., reduce and/or minimize) bubble formation in the liquid 816 and enable the liquid 816 to quickly settle (e.g., within 100-300 milliseconds) once the example container 700 decelerates to a stationary state.

One or more of the features, in whole or in part, of the containers 112, 114 in FIGS. 1-5 and the features in the container 700 of FIGS. 7 and 8 may be used in addition to or as an alternative to one or more of the features of one of the other containers.

Figure 9:
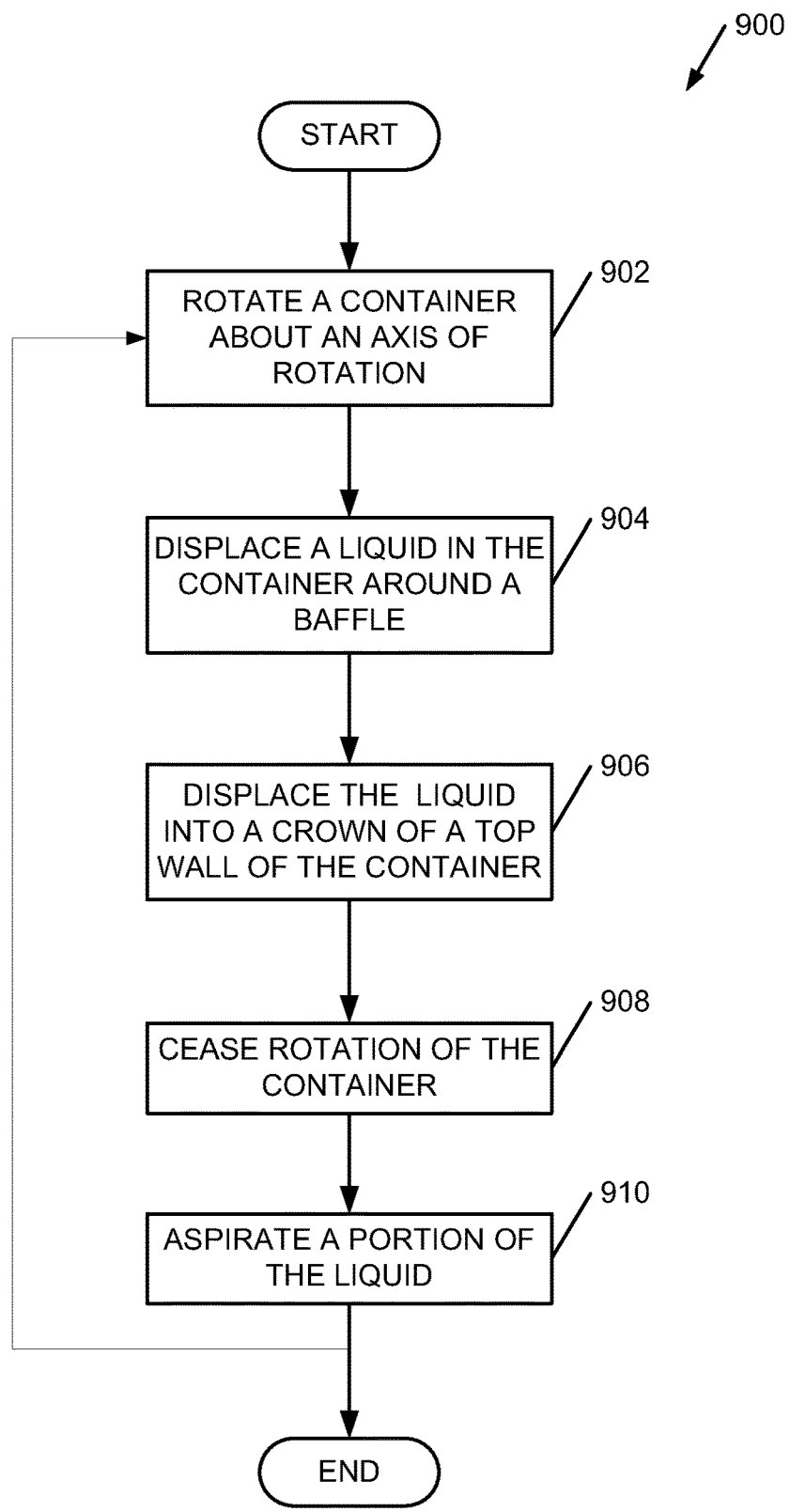
FIG. 9 is a flowchart representative of an example method disclosed herein.

A flowchart representative of an example method is shown in FIG. 9. Although the example method is described with reference to the flowchart illustrated in FIG. 9, many other methods may alternatively be used. For example, the order of execution of the blocks may be changed, and/or some of the blocks described may be changed, eliminated, or combined.

The example method 900 of FIG. 9 begins by rotating a container (e.g., the first container 112) about an axis of rotation such as, for example, the axis of rotation 106 of the carousel 102 (block 902). In some examples, the container moves from a first position to a second position via an acceleration or motion profile illustrated in the example graph 600 of FIG. 6. During rotation, liquid in the container 112 is displaced around a baffle (block 904). For example, the first liquid 400 in the first container 112 flows in a space between the first baffle 212 and the first sidewall 200, a space between the first baffle 212 and the second sidewall 202, and/or a space between the first baffle 212 and the first top wall 408. The baffles 212, 214, 216, 218 dampen the flow (e.g., sloshing) of the first liquid 400 to mitigate (e.g., decrease and/or substantially minimize) bubble formation in the first liquid 400.

The example process 900 also includes projecting or displacing the liquid into a crown of a top wall of the container (block 906). For example, the liquid 400 of the first container 112 is displaced into the first crown 414 during rotation. As a result, the first liquid 400 is prevented from flowing into the first throat 416 and out of the first container 112. The example process 900 also includes ceasing rotation of the container (block 908). In some examples, the baffles 212, 214, 216, 218 enable the first liquid 400 to settle after the rotation is ceased in approximately 100 to 300 milliseconds. The process 900 may also include, in some examples, aspirating a portion of the liquid (block 910), and then the process 900 may end or start over with rotation of the container about the axis (block 902)

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus, comprising:
a base;
a reagent container coupled to the base, the base configured to couple the reagent container to a rotatable carousel of a diagnostic analyzer, the reagent container to hold a liquid reagent to be used by the diagnostic analyzer for performing a diagnostic test on a sample, the reagent container comprising:
a first sidewall;
a second sidewall opposite the first sidewall;
a first end wall coupled between the first sidewall and the second sidewall;
a second end wall coupled between the first sidewall and the second sidewall opposite the first end wall;
a top wall coupled to and extending between the first sidewall, the second sidewall, the first end wall and the second end wall; and
a bottom wall opposite the top wall, the bottom wall coupled to the first sidewall, the second sidewall, the first end wall and the second end wall,
wherein the first sidewall, the second sidewall, the first end wall, the second end wall, the top wall and the bottom wall form a substantially enclosed volume,
wherein a first axis of the reagent container extends through the top wall and the bottom wall between the first sidewall and the second sidewall, and a second axis of the reagent container extends through the first sidewall and the second sidewall between the top wall and the bottom wall, the reagent container having a height along the first axis greater than a width along the second axis;
a first baffle extending from the bottom wall, the first baffle spaced apart from the first sidewall, the second sidewall, and the top wall such that the liquid reagent can flow between the first baffle and the first and second sidewalls; and
a second baffle extending from the bottom wall, the second baffle spaced apart from the first sidewall, the second sidewall and the top wall such that the liquid reagent can flow between the second baffle and the first and second sidewalls, the first and second baffles having c-shaped cross-sections, the first and second baffles spaced apart from each other and aligned along an axis extending between the first and second sidewalls.

2. The apparatus of claim 1, wherein the first baffle has a first height and the second baffle has a second height greater than the first height.

3. The apparatus of claim 1, wherein the top wall includes a first portion and a second portion, the first portion at a first height relative to the bottom wall and the second portion at a second height relative to the bottom wall greater than the first height, the first portion and the second portion connected by a non-vertical slope of the top wall.

4. The apparatus of claim 3, wherein the second portion defines an enclosed crown forming a cavity extending upward from an underside of the top wall to enable the liquid reagent to flow into the cavity when the reagent container is rotated.

5. The apparatus of claim 3, wherein the first baffle has a third height different than the first height and the second height.

6. The apparatus of claim 5, wherein the third height is greater than the first height.

7. The apparatus of claim 5, wherein the first baffle and the second baffle disposed radially relative to an axis of rotation of the apparatus.

8. The apparatus of claim 5, wherein the second baffle has a fourth height different than the first height, the second height and the third height.

9. The apparatus of claim 8, wherein the fourth height is less than the first height and the third height is greater than the first height.

10. The apparatus of claim 3, wherein the liquid reagent is disposed below the first height when the apparatus is stationary, and wherein a portion of the liquid reagent is disposed between the first height and the second height during rotation of the apparatus.

11. The apparatus of claim 3, wherein the first baffle extends a third height between the first height and the second height.

12. The apparatus of claim 3, wherein the first portion is in a first horizontal plane and the second portion is in a second horizontal plane different than the first horizontal plane.

13. The apparatus of claim 1, wherein the bottom wall is curved such that an end of the bottom wall is separated from the top wall by a first distance and a center of the bottom wall is separated from the top wall by a second distance, the second distance greater than the first distance.

14. The apparatus of claim 1, wherein the first baffle is spaced apart from the first end wall and the second end wall such that liquid reagent can flow between the first baffle and the first and second end walls.

15. The apparatus of claim 1, wherein a first distance between the first sidewall and the second sidewall adjacent the first end wall is less than a second distance between the first sidewall and the second sidewall adjacent the second end wall.

16. The apparatus of claim 15, wherein the first baffle is disposed closer to the first end wall than the second baffle.

17. The apparatus of claim 16, wherein the first baffle has a smaller cross-sectional size than the second baffle.

18. The apparatus of claim 15, wherein the first sidewall and the second sidewall are nonparallel.

19. The apparatus of claim 1, wherein a concave portion of the first baffle facing an axis of rotation of the reagent container.

20. The apparatus of claim 1, wherein the first baffle extends a first distance from the bottom wall and the second baffle extends a second distance from the bottom wall, the second distance less than the first distance.

21. The apparatus of claim 1, wherein the c-shaped cross-section of the second baffle has a larger radius than the c-shaped cross-section of the first baffle.

22. The apparatus of claim 1, wherein the first and second baffles reduce bubble formation in the liquid reagent as the liquid reagent moves in the reagent container.

23. The apparatus of claim 1, wherein the top wall includes an upward extending throat.

24. The apparatus of claim 23, further including a cap that is removably coupled to the throat.

25. The apparatus of claim 1, wherein the reagent container is a first reagent container, the bottom wall is a first bottom wall, and the top wall is a first top wall, further including:
a second reagent container coupled to the base adjacent the first reagent container, the second reagent container including a third baffle and a fourth baffle extending from a second bottom wall of the second reagent container, the third baffle and the fourth baffle spaced apart from a third sidewall, a fourth sidewall and a second top wall of the second reagent container such that a liquid can flow between the third and fourth baffles and the third and fourth sidewalls, the third and fourth baffles having c-shaped cross-sections, the third and fourth baffles spaced apart from each other and aligned along an axis extending between the third and second sidewalls.

26. The apparatus of claim 1, wherein the top wall includes an exterior surface having a first portion and a second portion, the first portion at a first height relative to the bottom wall and the second portion at a second height relative to the bottom wall greater than the first height.

27. A system comprising:
a reagent container including:
a first sidewall;
a second sidewall opposite the first sidewall;
a first end wall coupled between the first sidewall and the second sidewall;
a second end wall coupled between the first sidewall and the second sidewall opposite the first end wall;
a top wall coupled to and extending between the first sidewall, the second sidewall, the first end wall and the second end wall; and
a bottom wall opposite the top wall, the bottom wall coupled to the first sidewall, the second sidewall, the first end wall and the second end wall,
wherein the first sidewall, the second sidewall, the first end wall, the second end wall, the top wall and the bottom wall form a substantially enclosed volume,
wherein a first axis of the reagent container extends through the top wall and the bottom wall between the first sidewall and the second sidewall, and a second axis of the reagent container extends through the first sidewall and the second sidewall between the top wall and the bottom wall, the reagent container having a height along the first axis greater than a width along the second axis;
a liquid reagent contained in the reagent container to be used by a diagnostic analyzer for performing a diagnostic test on a sample;
a first baffle extending from the bottom wall, the first baffle spaced apart from the first sidewall, the second sidewall, and the top wall such that the liquid reagent can flow between the first baffle and the first and second sidewalls;
a second baffle extending from the bottom wall, the second baffle spaced apart from the first sidewall, the second sidewall and the top wall such that the liquid reagent can flow between the second baffle and the first and second sidewalls, the first and second baffles having c-shaped cross-sections, the first and second baffles spaced apart from each other and aligned along an axis extending between the first and second sidewalls; and
a carousel, the reagent container disposed on the carousel and rotated about an axis of rotation of the carousel, wherein, when the reagent container is disposed on the carousel, the first baffle and the second baffle are positioned radially relative to the axis of rotation of the carousel.

28. An apparatus for use in a diagnostic analyzer, the apparatus comprising:
a base configured to be coupled to a rotatable carousel of the diagnostic analyzer; and
a container coupled to the base, the container including:
a first sidewall;
a second sidewall opposite the first sidewall;
a first end wall coupled between the first sidewall and the second sidewall;
a second end wall coupled between the first sidewall and the second sidewall opposite the first end wall;
a top wall coupled to and extending between the first sidewall, the second sidewall, the first end wall and the second end wall;
a bottom wall opposite the top wall, the bottom wall coupled to the first sidewall, the second sidewall, the first end wall and the second end wall,
wherein the first sidewall, the second sidewall, the first end wall, the second end wall, the top wall and the bottom wall form a substantially enclosed volume,
wherein a first axis of the container extends through the top wall and the bottom wall between the first sidewall and the second sidewall, and a second axis of the container extends through the first sidewall and the second sidewall between the top wall and the bottom wall, the container having a height along the first axis greater than a width along the second axis;
a first baffle extending from the bottom wall, the first baffle spaced apart from the first sidewall, the second sidewall, and the top wall; and
a second baffle extending from the bottom wall, the second baffle spaced apart from the first sidewall, the second sidewall, the top wall and the first baffle, the first and second baffles positioned equidistant from the first and second sidewalls.

29. The apparatus of claim 28, wherein the first and second baffles have c-shaped cross-sections having substantially the same radius of curvature.

30. The apparatus of claim 28, wherein the first and second baffles are to reduce bubble formation in a liquid as the liquid moves in the container.

* * * * *